(12) United States Patent
Mermet

(10) Patent No.: US 11,629,790 B2
(45) Date of Patent: Apr. 18, 2023

(54) PINCH CLAMP DEVICE

(71) Applicant: Fresenius Vial SAS, Brézins (FR)

(72) Inventor: Emeric Mermet, Saint Martin le Vinoux (FR)

(73) Assignee: Fresenius Vial SAS, Brézins (FR)

( * ) Notice: Subject to any disclaimer, the term of this patent is extended or adjusted under 35 U.S.C. 154(b) by 129 days.

(21) Appl. No.: 16/643,739

(22) PCT Filed: Aug. 24, 2018

(86) PCT No.: PCT/EP2018/072849
§ 371 (c)(1),
(2) Date: Mar. 2, 2020

(87) PCT Pub. No.: WO2019/048255
PCT Pub. Date: Mar. 14, 2019

(65) Prior Publication Data
US 2020/0398041 A1    Dec. 24, 2020

(30) Foreign Application Priority Data
Sep. 11, 2017 (EP) .................................. 17306167

(51) Int. Cl.
*F16K 7/06* (2006.01)
*A61M 39/28* (2006.01)

(52) U.S. Cl.
CPC ........... *F16K 7/065* (2013.01); *A61M 39/281* (2013.01); *A61M 2205/6081* (2013.01)

(58) Field of Classification Search
CPC .............. A61M 39/281; A61M 39/285; A61M 39/286; A61M 39/287; A61M 39/28;
(Continued)

(56) References Cited

U.S. PATENT DOCUMENTS 492,580 A * 2/1893 Hadley ................... B60C 29/02
                                                         152/427
2,825,333 A * 3/1958 Broman .............. A61M 39/284
                                                         604/412
(Continued)

FOREIGN PATENT DOCUMENTS

EP         1466646 A1    10/2004
GB         2448374 A     10/2008
WO   WO2010/101783 A2    9/2010

OTHER PUBLICATIONS

International Search Report and Written Opinion, counterpart International Appl. No. PCT/EP2018/072849 (dated Sep. 28, 2018) (13 pages).

*Primary Examiner* — Kevin F Murphy
*Assistant Examiner* — Jonathan J Waddy
(74) *Attorney, Agent, or Firm* — Cook Alex Ltd.

(57) ABSTRACT

A pinch clamp device for a flexible tube is disclosed, the pinch clamp device comprising a first part (2) and a second part (3) that are movable with respect to each other, wherein the first part (2) comprises a first conduit (5) for housing a flexible tube and the second part (3) comprises a second conduit (6) for housing the same flexible tube, wherein the first part (2) and the second part (3) are arranged in an interacting manner such that the pinch clamp device can be present in a first position or in a second position, wherein a flow of a fluid within a flexible tube arranged inside the first conduit (5) and the second conduit (6) is enabled in the first position, and wherein a flow of a fluid within a flexible tube arranged inside the first conduit (5) and the second conduit (6) is prevented in the second position. According to an aspect of the invention, the first part (2) and the second part (3) are designed axisymmetrically. Furthermore, a pinch clamp arrangement comprising such a pinch clamp device is (Continued)

disclosed. Additionally pump arrangement comprising a pump and such a pinch clamp arrangement is disclosed.

12 Claims, 2 Drawing Sheets

(58) Field of Classification Search
CPC . F16K 7/06; F16K 7/065; F16K 7/066; F16K 7/00; F16K 7/02; F16K 7/04
USPC .......................................................... 251/4, 8
See application file for complete search history.

(56) References Cited

U.S. PATENT DOCUMENTS

| | | | | |
|---|---|---|---|---|
| 2,858,095 A | | 10/1958 | Harris et al. | |
| 3,497,175 A | * | 2/1970 | Koland | A61M 39/284 251/9 |
| 3,544,060 A | * | 12/1970 | Demler, Sr. | B01L 3/567 251/9 |
| 3,612,474 A | * | 10/1971 | Strohl, Jr. | A61M 39/284 251/9 |
| 4,136,694 A | * | 1/1979 | Kuehn | A61M 39/221 604/412 |
| 4,586,691 A | * | 5/1986 | Kozlow | A61M 39/281 251/7 |
| 4,609,300 A | * | 9/1986 | Robert | B65D 51/32 132/218 |
| 5,704,584 A | * | 1/1998 | Winterer | A61M 39/281 251/7 |
| 5,810,323 A | | 9/1998 | Winterer et al. | |
| 6,142,979 A | * | 11/2000 | McNally | A61M 39/281 248/68.1 |
| 6,749,591 B1 | * | 6/2004 | McNally | A61M 39/281 211/60.1 |
| 2010/0056976 A1 | * | 3/2010 | Howard | A61M 1/3656 604/6.16 |
| 2010/0234809 A1 | * | 9/2010 | Kenley | F16K 7/06 604/180 |
| 2010/0268161 A1 | | 10/2010 | Traversaz | |
| 2020/0008898 A1 | * | 1/2020 | Rousche | A61B 5/1422 |
| 2020/0108236 A1 | * | 4/2020 | Salazar | A61M 29/00 |

* cited by examiner

PINCH CLAMP DEVICE

The present application is a U.S. National Stage of PCT International Patent Application No. PCT/EP2018/072849, filed Aug. 24, 2018, which claims priority to EP Application No. 17306167, filed Sep. 11, 2017, both of which are hereby incorporated herein by reference.

The present invention relates to a pinch clamp device according to the preamble of claim 1, to a pinch clamp arrangement comprising such a pinch clamp device according to the preamble of claim 11, and to a pump arrangement comprising such a pinch clamp arrangement according to the preamble of claim 12.

BACKGROUND

A so-called pump set, i.e., a combination of a flexible tube and a pinch clamp (and optionally connecting parts) is inserted into a pump device, such as a volumetric pump, in order that the pump device can pump a fluid through the tube. Thereby, the pinch clamp is intended to prevent free flow of a fluid through the flexible tube if the pump set is removed from the pump device or if the pump device is opened.

US 2010/0268161 A1 discloses a clamp for a flexible tube that is intended to be inserted into a pump device. However, there is only one geometric arrangement (one specific angle) in which the disclosed clamp can be inserted into the pump device. This complicates installing of the clamp (or a pump set equipped therewith) into the pump device and results in extended handling times for healthcare professionals.

It is an object of the present invention to provide a pinch clamp that can be more intuitively handled than pinch clamps known from prior art.

SUMMARY

This object is achieved with a pinch clamp device for a flexible tube having the claim elements of claim 1. Such a pinch clamp device comprises a first part and a second part. Both parts are movable with respect to each other. Thereby, the first part comprises a first conduit for housing a flexible tube. Likewise, the second part comprises a second conduit for housing the same flexible tube. The first part and the second part interact with each other. Specifically, depending on the relative position of the first part and the second part, the pinch clamp device can be present in a first position or in a second position. Thereby, a flow of fluid within a flexible tube arranged inside the first conduit and inside the second conduit is enabled in the first position. Contrary, a flow of fluid within a flexible tube arranged inside the first conduit and inside the second conduit is prevented in the second position. By moving the first part and the second part relative to each other, the pinch clamp device can be transferred from its first position to its second position, and vice versa. Thus, it is possible to open and close the pinch clamp by such a movement of the first part and the second part.

The first part and the second part of the claimed pinch clamp device are designed axisymmetrically. In doing so, it is not necessary to install the pinch clamp device in a specific geometric arrangement or in a specific angle into a pump device. Rather, any orientation of the pinch clamp device is likewise suited for the pinch clamp device to be installed into a pump. Thus, the user of the pinch clamp device needs no longer to look for the "correct" orientation of the pinch clamp so that it can be installed into a corresponding pump device. Rather, the user can simply install the pinch clamp device in the orientation in which he or she currently holds it in his or her hands. Therewith, the use of the pinch clamp device according to an aspect of the instant invention is much more intuitive than the use of a pinch clamp device known from prior art. Furthermore, the handling time for installing a pump set comprising a corresponding pinch clamp device is significantly reduced compared to the handling time of pinch clamp devices known from prior art. This saved time can be used by healthcare professionals for patient care itself.

In an embodiment, a symmetry axis of the first part extends along the first conduit. Alternatively or additionally, a symmetry axis of the second part extends along the second conduit. Thus, in this embodiment, the first conduit is located in the symmetry center of the first part, and/or the second conduit is located in the symmetry center of the second part. In an embodiment, the first part and the second part share the same symmetry axis. If both conduits are located in the symmetry center of the respective part, a flexible tube is guided through the first conduit and the second conduit always in the same position, irrespective of the specific geometric arrangement of the first part and the second part. This makes an installation of a pump set comprising a corresponding pinch clamp device particularly simple.

It should be noted that the pinch clamp needs not be necessarily used together with a pump. Rather, it is suited to be used for clamping any kind of conduit. E.g., it can also be used for clamping a conduit through which a fluid flows by gravity in order to stop the fluid flow as desired.

In an embodiment, the first part and the second part are movable with respect to each other by a translational movement of at least one of the parts. Thus, it is possible to move either the first part or the second part, or both the first part and the second part in a translational manner. In other embodiments, a rotational movement or a combination of a rotational movement and a translational movement (e.g., a helical movement along a helical guiding) are also possible.

In an embodiment, the second part can be moved along an extension direction of the first conduit. In a particular appropriate variant of this embodiment, the first conduit and the second conduit are arranged coaxially to each other.

In an embodiment, the first part and the second part are individual components that interact with each other but could be generally separated. This facilitates the manufacturing of the pinch clamp device. However, in an embodiment, the first part and the second part act cooperate with each other, wherein they cannot be separated from each other when exerting forces that are applied during normal use of the pinch clamp device. Thus, only upon exerting forces exceeding the forces applied during intended use of the pinch clamp device, the first part could be separated from the second part.

In an embodiment, the second part is nested within the first part. E.g., it is possible that the second part can be inserted into the first part and at least partly withdrawn from the first part in a telescopic manner. Such an arrangement makes an application of the pinch clamp device particularly simple.

In an embodiment, the second part comprises a flexible extension extending along the second conduit. Thereby, the flexible extension can be present in a relaxed position or in a compressed position. If the flexible extension is in its relaxed position, then the pinch clamp device is in its first position. If the flexible extension is in its compressed position, the pinch clamp device is in its second position. In an embodiment, the flexible extension is that part of the second part that can be inserted into the first part and that can be partly withdrawn from the first part. In an embodiment, the flexible extension is in its relaxed state if the second part is fully inserted into the first part. Then, the flexible extension is in its compressed position if the second part is partly withdrawn from the first part up to its maximum withdrawn position with respect to the first part.

In an embodiment, the flexible extension has a free end and comprises a protrusion on the free end. Thereby, this protrusion extends readily away from the second conduit. This protrusion is received in a recess in the first part if the flexible extension is in its relaxed position (e.g., if the second part is fully inserted into the first part). Likewise, if the flexible extension is in its compressed position, the protrusion abuts an inner wall of the first conduit (e.g., if the second part is at least partly withdrawn from the first part, but is still partly nested within the first part).

In an embodiment, the second part comprises a mark that is only visible for a user of the pinch clamp device if the pinch clamp device is in its second position. Such a mark facilitates a recognition whether or not the pinch clamp device it in its first (open) or second (closed) position. The marker can, e.g., be realized by a color coding. If a user of the pinch clamp device sees the color coding or any other kind of marker, he or she will immediately know that the pinch clamp device it is in its second (closed) position so that no free flow of a fluid being present with in a flexible tube that is received by the pinch clamp device is possible. At the same time, the user will immediately know that he or she will have to transfer the pinch clamp device into its first (open) position in order to allow a flow of fluid through a flexible tube being received within the pinch clamp device. Thus, for proper operation of a pump device in which the pinch clamp device is installed, the marker has to disappear from the visual field of the user. Expressed in other words, the marker, e.g. a color coding, allows a visual identification of the open or closed state of the pinch clamp device.

In an embodiment, the first part and the second part have a different outer design or geometry. Then, it is particularly easy for a user to install the pinch clamp device or a pump set including such a pinch clamp device in the correct upstream/downstream orientation within a pump. This additional aid for a user to correctly install the pinch clamp device within a pump device makes particularly sense if a corresponding pump set has a defined inflow and outflow orientation of a fluid to be transported through the pump set. Pump sets usually exhibit such an orientation. The outer design of the first part and the second part can be chosen such that it is immediately apparent for a user which part of the pinch clamp device is to be inserted into the corresponding recess in a pump device. Since the first part and the second part are designed axisymmetrically, the specific orientation of the first part and the second part does not matter for correct installation if both parts are orientated to the correct direction for the installation of the pinch clamp device.

In an aspect, the present invention relates to a pinch clamp arrangement comprising a pinch clamp device according to the preceding explanations as well as a flexible tube. Thereby, the pinch clamp device comprises a first part and a second part. Both parts are movable with respect to each other. The first part comprises a first conduit that houses a section of the flexible tube. The second part comprises a second conduit that also houses a section of the flexible tube. Thereby, the first part and the second part are arranged in interacting manner so that the pinch clamp device can be present in a first position or in a second position. If it is in the first position, flow of fluid within the flexible tube is enabled. If the device is in its second position, a flow of fluid within the flexible tube is prevented. To allow an easy and intuitive installation of the pinch clamp device of the pinch clamp arrangement, the first part and the second part are designed axisymmetrically.

The pinch clamp arrangement can also be referred to as pump set, in particular if it additionally comprises connecting elements at the respective ends of the flexible tube.

In an aspect, the present invention also relates to a pump arrangement comprising a pump device and a pinch clamp arrangement according to the preceding explanations, wherein the pinch clamp arrangement is installed into the pump.

In an embodiment, the pump device comprises a cover that can be opened to install the pinch clamp arrangement within the pump or to remove it therefore. Thereby, the pinch clamp device is automatically transferred from its first position into its second position if the cover of the pump device is opened or if the pinch clamp arrangement is removed from the pump device. This automatic transfer can be realized by a lever being activated by said cover and interacting with the pinch clamp arrangement such that it causes a movement of the second part relative to the first part of the pinch clamp device.

In an embodiment, the pump is a volumetric pump, e.g., a perfusion pump that can be used to administer a pharmaceutical composition or a nutritional composition to a person in need thereof.

In an aspect, the present invention relates to a method for administering a pharmaceutical composition or a nutritional composition to person in need thereof by inserting a pinch clamp arrangement according to the preceding explanations into a pump device, connecting a first end of the flexible tube of the pinch clamp arrangement to a reservoir of a pharmaceutical composition or a nutritional composition, and connecting a second end of the flexible tube to a cannula or feeding tube which is then used to administer the pharmaceutical composition or the nutritional composition to a person in need thereof.

All embodiments described in the preceding sections with respect to the pinch clamp device can be combined in any desired manner and can be transferred to the described pinch clamp arrangement, the described pump arrangement, and the described method, and vice versa.

BRIEF DESCRIPTION OF THE DRAWINGS

Further details of aspects of the present invention will be explained with respect to exemplary embodiment and accompanying Figures. In the Figures.

DETAILED DESCRIPTION OF THE EMBODIMENTS

Figure 1:
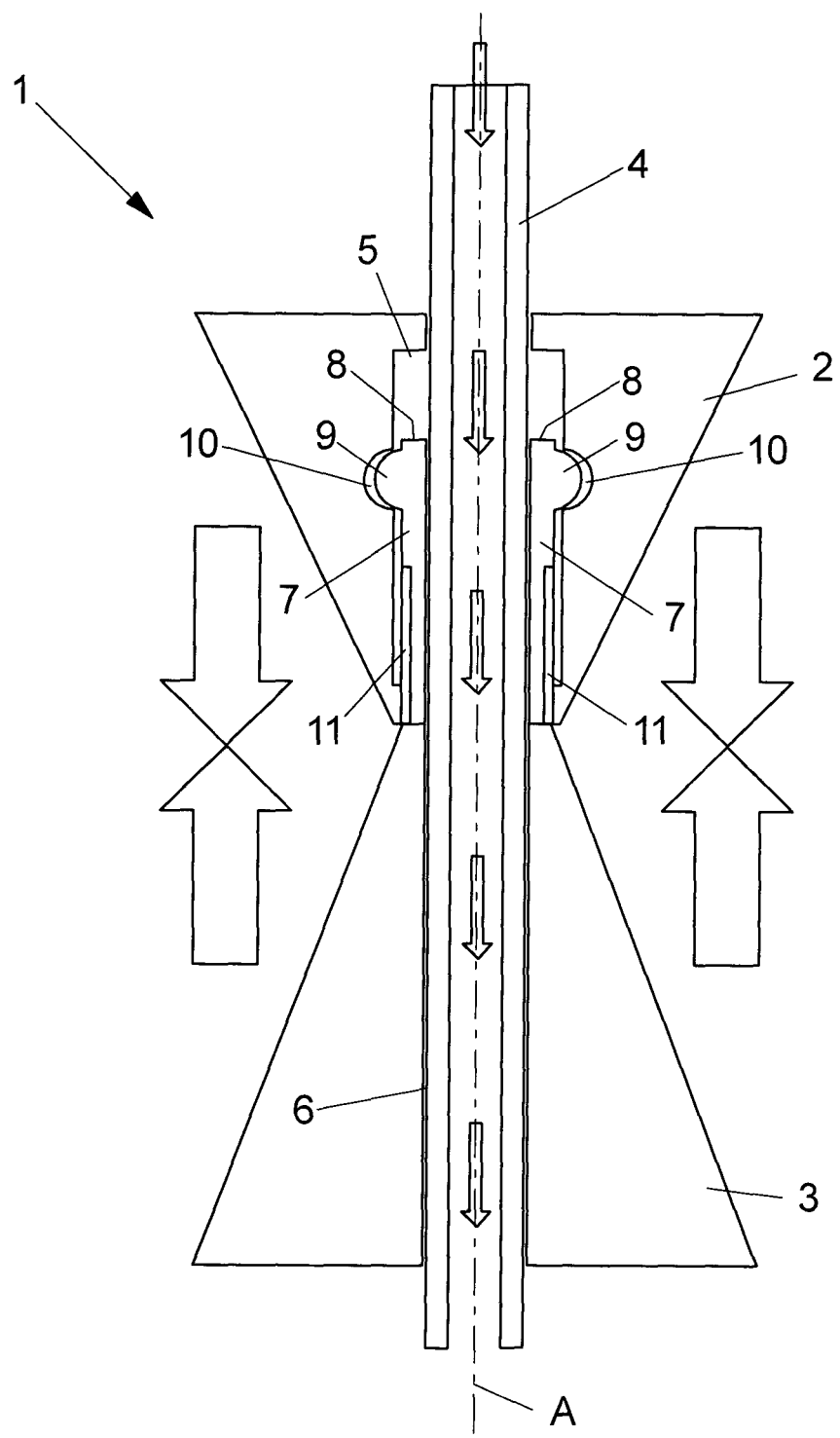
FIG. 1 shows a cross-sectional view of an embodiment of a pinch clamp device in a first (open) position.

FIG. 1 shows a pinch clamp arrangement 1 that comprises a first part 2, a second part 3 and a flexible tube for extending through the first part 2 and the second part 3. The first part 2 and the second part 3 have a cone-like outer geometry. They are designed axisymmetrically with respect to a symmetry axis A extending along the center of a first conduit 5 and a second conduit 6. Thereby, the first conduit 5 is arranged in the center of the first part 2, and the second conduit 6 is arranged in the center of the second part 3.

A flexible tube 4 is guided through the first conduit 5 and the second conduit 6 so as to be encompassed by the first part 2 and the second part 3 of the pinch clamp arrangement 1.

The second part 3 comprises besides its conical body two flexible fingers 7 that serve as flexible extension. These flexible fingers 7 extend away from the conical body along the second conduit 6. The flexible fingers 7 can be moved in a radial direction, i.e., towards the symmetry axis A.

The flexible fingers have a free end 8 and a protrusion 9 that is arranged near the flexible end 8. This protrusion is housed in a recess 10 of the first part 2 of the pinch clamp arrangement 1. Thereby, the recess 10 is dimensioned such that the protrusion 9 of each flexible finger 7 can be housed in the recess 10 without bending the flexible finger 7 towards the symmetry axis A.

On an outer circumference of the flexible fingers 7, a color coding 11 serving as a mark is arranged. This color coding 11 is invisible if the pinch clamp arrangement 1 is in its first position illustrated in FIG. 1 since the second part 3 is, in this position, inserted into the first part 2 to such an extent that the color coding 11 is fully received within the interior of the first part 2.

Since the flexible fingers 7 are not bent towards the symmetry axis A, the cross-section of the flexible tube 4 is not altered within the first conduit 5 and the second conduit 6 so that any fluid flowing through the flexible tube 4 can freely pass the first part 2 and the second part 3 of the pinch clamp arrangement 1. This is illustrated by corresponding arrows along the symmetry axis A.

Figure 2:
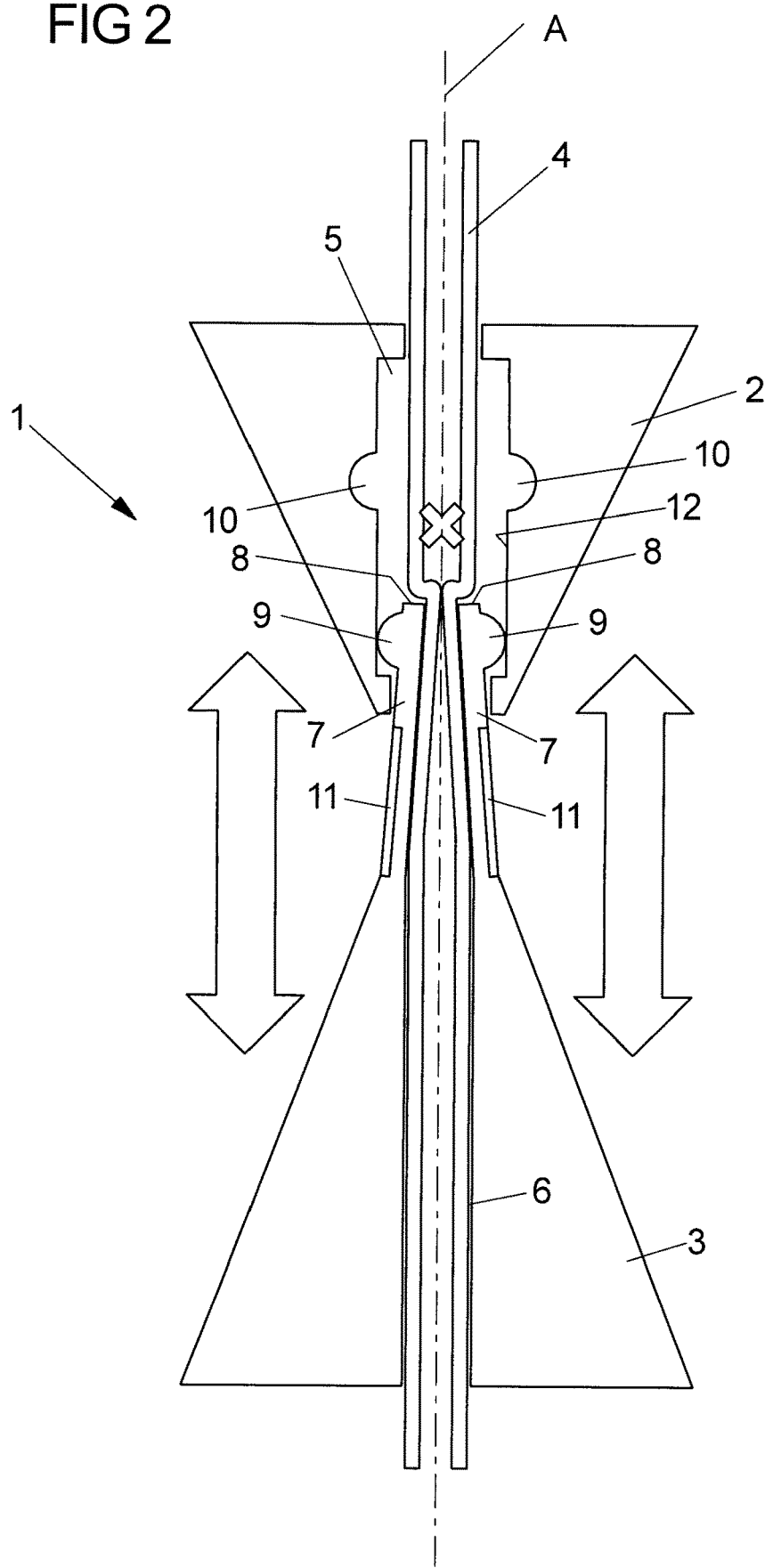
FIG. 2 shows a cross-sectional view of the pinch clamp device of FIG. 1 in its second (closed) position.

FIG. 2 shows the pinch clamp arrangement 1 of FIG. 1 in its second (closed) position. The same elements are marked with the same numeral references as in FIG. 1. In this second position, the second part 3 is partly withdrawn from the first part 1 (although it still interacts with the first part 2). Due to this partial withdrawal, the protrusions 9 are no longer received by the recesses 10. Rather, the protrusions 9 abut an inner wall 12 of the first conduit 5. Due to this, the flexible fingers 7 are bent towards the symmetry axis A. As a consequence, the flexible fingers 7 press against the flexible tube 4 and prevent flow of fluid within the flexible tube 4. Thus, in this position, the pinch clamp arrangement 1 securely prevents any free flow of fluid through the flexible tube 4.

Since the second part 3 is partly withdrawn from the first part 2 in the direction indicated by big arrows at the side of the first part 2 and the second part 3, the color coding 11 becomes visible for a user. Thus, the user can see at a glance that the pinch clamp arrangement 1 is in its closed position and does not allow any fluid flowing through the flexible tube 4. If the user intends to enable a fluid flow, he or she has to move the first part 2 and the second part 3 in the direction of the arrows indicated in FIG. 1 at the side of the first part 2 and the second part 3.

The invention claimed is:

1. A pinch clamp device for a flexible tube, comprising:
    a first part and a second part that are movable with respect to each other,
    wherein the first part comprises a first conduit for housing the flexible tube and the second part comprises a second conduit for housing the flexible tube, the second part nested within the first part and the second part moveable along an extension direction of the first conduit and the first conduit having an inner wall with a smooth cylindrical surface except for a recess shaped in the smooth surface,
    wherein the first part and the second part are arranged in an interacting manner such that the pinch clamp device can be present in a first position and in an alternative second position, wherein a flow of a fluid within the flexible tube arranged inside the first conduit and the second conduit is enabled in the first position, and a flow of a fluid within the flexible tube arranged inside the first conduit and the second conduit is prevented in the second position,
    wherein the second part comprises a flexible extension extending along the second conduit, wherein the flexible extension can be present in a relaxed position and in an alternative compressed position, wherein the pinch clamp device is in the first position if the flexible extension is in its relaxed position, and wherein the pinch clamp device is in the second position if the flexible extension is in its compressed position;
    wherein the flexible extension has a free end and a protrusion on the free end, wherein the protrusion extends radially away from the second conduit, wherein the protrusion is received in the recess shaped in the smooth surface of the inner wall of the first conduit of the first part if the flexible extension is in the relaxed position and abuts the smooth surface of the inner wall of the first conduit if the flexible extension is in the alternative compressed position; and
    wherein the first part and the second part are designed axisymmetrically.

2. The pinch clamp device according to claim 1, wherein a symmetry axis of the first part extends along the first conduit and/or a symmetry axis of the second part extends along the second conduit.

3. The pinch clamp device according to claim 1, wherein the first part and the second part are movable with respect to each other by a translational movement of at least one of the first part and the second part.

4. The pinch clamp device according to claim 1, wherein the first part and the second part are individual components.

5. The pinch clamp device according to claim 1, wherein the second part comprises a mark that is only visible for a user of the pinch clamp device if the pinch clamp device is in its second position.

6. The pinch clamp device according to claim 1, wherein the first part and the second part have a different outer design.

7. The pinch clamp device according to claim 1, wherein the pinch clamp device is unbiased toward the first position or the second position.

8. A pinch clamp arrangement comprising a pinch clamp device and a flexible tube,
    wherein the pinch clamp device comprises a first part and a second part that are movable with respect to each other,
    wherein the first part comprises a first conduit that houses a section of the flexible tube, and the second part comprises a second conduit that houses a section of the flexible tube, the second part nested within the first part and the second part moveable along an extension direction of the first conduit and the first conduit having an inner wall with a smooth cylindrical surface except for a recess shaped in the smooth surface,
    wherein the first part and the second part are arranged in an interacting manner such that the pinch clamp device can be present in a first position and in an alternative second position, wherein a flow of a fluid within the flexible tube is enabled in the first position, and a flow of a fluid within the flexible tube is prevented in the second position, wherein the second part comprises a flexible extension extending along the second conduit, wherein the flexible extension can be present in a relaxed position and in an alternative compressed position, wherein the pinch clamp device is in the first position if the flexible extension is in its relaxed position, and wherein the pinch clamp device is in the second position if the flexible extension is in its compressed position, wherein the flexible extension has a free end and a protrusion on the free end, wherein the protrusion extends radially away from the second conduit, wherein the protrusion is received in the recess shaped in the smooth surface of the inner wall of the first conduit of the first part if the flexible extension is in the relaxed position and abuts the smooth surface of the inner wall of the first conduit if the flexible extension is in the alternative compressed position, and wherein the first part and the second part are designed axisymmetrically.

9. A pump arrangement comprising a pump and a pinch clamp arrangement according to claim 8 that is installed into the pump.

10. The pump arrangement according to claim 9, wherein the pump is a volumetric pump.

11. The pump arrangement according to claim 9, wherein the pump is a perfusion pump.

12. The pump arrangement according to claim 8, wherein the pinch clamp device is unbiased toward the first position or the second position.

* * * * *